United States Patent
Clark et al.

(10) Patent No.: US 9,579,355 B1
(45) Date of Patent: Feb. 28, 2017

(54) COMPOSITION AND METHOD OF TREATING ACTINIC PURPURA

(71) Applicant: Clark Pharmaceuticals LLC, Fort Worth, TX (US)

(72) Inventors: Stephen W. Clark, Fort Worth, TX (US); Natalie Barger, Fort Worth, TX (US)

(73) Assignee: Clark Pharmaceuticals LLC, Fort Worth, TX (US)

( * ) Notice: Subject to any disclaimer, the term of this patent is extended or adjusted under 35 U.S.C. 154(b) by 326 days.

(21) Appl. No.: 14/040,169

(22) Filed: Sep. 27, 2013

Related U.S. Application Data

(60) Provisional application No. 61/744,943, filed on Oct. 5, 2012.

(51) Int. Cl.

| | | |
|---|---|---|
| *A61K 36/185* | (2006.01) | |
| *A61K 36/28* | (2006.01) | |
| *A61K 36/48* | (2006.01) | |
| *A61K 31/122* | (2006.01) | |
| *A61K 31/19* | (2006.01) | |
| *A61K 31/56* | (2006.01) | |

(52) U.S. Cl.
CPC ............ *A61K 36/28* (2013.01); *A61K 31/122* (2013.01); *A61K 31/19* (2013.01); *A61K 31/56* (2013.01)

(58) Field of Classification Search
CPC ....... A61K 36/185; A61K 36/28; A61K 36/48
USPC .................................. 424/725, 757
See application file for complete search history.

(56) References Cited

U.S. PATENT DOCUMENTS

| | | | | |
|---|---|---|---|---|
| 5,510,391 A | * | 4/1996 | Elson | A61K 8/67 514/681 |
| 5,641,480 A | * | 6/1997 | Vermeer | A61K 8/046 424/70.1 |
| 6,630,163 B1 | * | 10/2003 | Murad | A61K 8/97 424/401 |
| 7,029,711 B2 | * | 4/2006 | Farrell | A61K 36/185 424/522 |
| 8,367,122 B2 | * | 2/2013 | Stephens | A61K 31/198 424/401 |
| 2002/0127256 A1 | * | 9/2002 | Murad | A61K 8/365 424/401 |
| 2003/0007939 A1 | * | 1/2003 | Murad | A61K 8/22 424/61 |
| 2004/0009142 A1 | * | 1/2004 | Zambaux | A61K 8/34 424/74 |
| 2006/0074029 A1 | * | 4/2006 | Leece | A61K 8/34 514/23 |
| 2009/0104292 A1 | * | 4/2009 | Alam | A61K 36/00 424/725 |
| 2010/0310654 A1 | * | 12/2010 | Jacono | A61K 36/28 424/474 |
| 2011/0293696 A1 | * | 12/2011 | Fein | A61K 9/2009 424/450 |
| 2012/0305415 A1 | * | 12/2012 | Gleyzer | A45D 34/00 206/220 |
| 2014/0031422 A1 | * | 1/2014 | Fein | A61K 9/2009 514/456 |

\* cited by examiner

*Primary Examiner* — Chris R Tate
(74) *Attorney, Agent, or Firm* — Phillips Murrah PC; Martin G. Ozinga

(57) ABSTRACT

The present invention is a composition and method of treatment for actinic purpura, skin disorders, and skin conditions in general through topical systematic and periodic application of a formulation that generally may include ingredients to improve circulation such as but not limited to *arnica* oil CLR and phytotonine; ingredients to thicken the skin such as but not limited to retistar, glycolic acid, vitamin K1, and phyto-age; and ingredients to repair the skin's barrier, such as but not limited to timecode, SKINMIMICS, ABS pomegranate sterols, and pentatavitin.

1 Claim, No Drawings

COMPOSITION AND METHOD OF TREATING ACTINIC PURPURA

CROSS-REFERENCE TO RELATED APPLICATIONS

Priority is claimed from provisional patent application U.S. Ser. No. 61/744,943 filed on Oct. 5, 2012 and incorporated by reference herein.

BACKGROUND OF THE INVENTION

1. Field of the Invention

In general, the present invention is a composition and method of treatment for actinic purpura, skin disorders, and skin conditions in general. More in particular, the present invention is a systematic and periodic application of a topical formulation that may include ingredients to improve circulation such as but not limited to arnica oil CLR and phytotonine; ingredients to thicken the skin such as but not limited to retistar, glycolic acid, vitamin K1, and phyto-age; and ingredients to repair the skin's barrier, such as but not limited to timecode, SKINMIMICS, ABS pomegranate sterols, and pentatavitin.

2. Description of the Prior Art

Mature skin is often prone to pronounced bruising due to decreased blood flow, reduction in connective tissue (i e thinning skin), loss of subcutaneous fat to support the skin structure, and flattening of the Dermal-Epidermal Junction and effacement of the dermal papillae. This condition is referred to as solar or actinic purpura. Although the lesions are not typically associated with any serious complications, bruising may be cosmetically distressing and may leave dyspigmentation or scarring.

Actinic purpura is a benign clinical entity resulting from sun-induced damage to the connective tissue of the dermis. It is characterized by ecchymoses on the surfaces of the forearms and the dorsa of the hands that usually last 1-3 weeks. The condition was first described in 1818 when a physician named Bateman noted dark purple blotches and determined that they were due to the extravasation of blood into the dermal tissue. Hence, it is sometimes called Bateman purpura. It is common in elderly individuals and usually occurs after unrecognized minor trauma to the respective areas.

Clinical aspects of dermatoporosis include morphological markers of fragility, such as senile purpura, stellate pseudoscars, and skin atrophy. The concept of the syndrome term dermatoporosis has been used to compare it to osteoporosis, implying both should be prevented and treated to avoid complications The purple macules and patches of this condition occur because red blood cells leak into the dermal tissue. This extravasation is secondary to the fragility of the blood vessel walls caused by ultraviolet radiation-induced dermal tissue atrophy. This atrophy renders the skin and microvasculature more susceptible to the effects of minor trauma and shearing forces. The insult to the skin is typically so minor that isolating it as a cause of the bruise can be difficult. Notably, no inflammatory component is found in the dermal tissue. The absence of a phagocytic response to the extravascular blood has been postulated to be responsible for delaying resorption for as long as 3 weeks.

Actinic purpura may be, along with osteoporosis, a sign of collagen loss in skin and bone. This causal loss of skin collagen has been confirmed when collagen was expressed absolutely, instead of as a percentage or ratio. That is, women have less collagen than men and it decreases by 1% a year in exposed and unexposed skin. These changes in skin collagen may correspond to changes in bone density. The hypothesis is that the changes in skin collagen also occur in bone collagen, leading to the associated changes in bone density.

Actinic purpura does not require extensive medical care. To prevent further ultraviolet-induced damage to the skin, sunscreens that provide both UV-A and UV-B protection should be applied daily, especially to areas affected by the purpuric lesions. Patients should also use barrier protection.

Actinic purpura is an extremely common finding in elderly individuals, occurring in approximately 11.9% of those older than 50 years. Its prevalence markedly increases with years of exposure to the sun. Furthermore, a study of the prevalence of dermatoses in 75 elderly residents in a long-term care facility in Santos, Brazil, found 280 dermatoses, with an average number of 3.73 per elderly person and 32 different types of dermatoses. Actinic purpura was evident in 29.3% of them.

Chronic sun exposure leads to skin changes that predispose patients to actinic purpura. Because of the ultraviolet-induced atrophy, the connective tissue of the dermis is no longer able to adequately support the microvasculature. As a result, even minor trauma can tear the blood vessels, leading to the extravasation of blood. The effects of chronic sun exposure with the resultant ultraviolet radiation induced skin changes more often and are more pronounced in fair-skinned individuals than in others.

Both sexes are equally affected, but typically, actinic purpura occurs almost exclusively in the elderly population, though it may sporadically occur in younger people. The incidence varies with respect to age. Approximately 2% of those aged 60-70 years and as many as 25% of those aged 90-100 years can have the purpuric lesions.

Often patients may report the appearance of purple blotches or bruises on their forearms, hands, face, or neck. The macules are not associated with pain or pruritus. Patients also may report a history of the lesions resolving and then subsequently reappearing. Residual brown pigmentation may appear after the purpuric macules resolve. Individual lesions usually last 1-3 weeks, and they do not undergo the color changes that occur with other types of purpuric lesions. Further, patients are typically unaware of any external trauma that may have been responsible for the bruising. Still further, individuals may report a history of chronic sun exposure to skin sites where lesions are present.

Purpuric patches and macules larger than 3 mm in diameter are usually present on the extensor surfaces of the forearms and on the dorsa of the hands; the lesions do not extend onto the fingers. Bruising may also be found on the neck and face. Macules and patches are dark purple and irregularly shaped. A sharp margin is seen between the borders of the lesions and the surrounding skin. Some macules are more deeply colored than other are because the duration of the lesions varies. The color changes that are typically associated with actinic purpura or bruising due to other causes do not occur, although residual brown pigmentation may persist.

Lesions of actinic purpura occur in areas of atrophic and inelastic photo damaged skin. Other signs of dermatoheliosis often present include leathered wrinkling, stellate pseudoscars, and a sallow yellow hue to the skin. Lentigines and scars may be present. The skin may appear darker secondary to hyperpigmentation due to hemosiderosis.

Of note, the US total skin care market was estimated at $8.3 billion in 2008, up 1.1% over 2007. From 2003 to 2008, the market for premium skin care products grew 18% or a compounded annual growth rate of 3.4%. Contributing to this growth was the anti-aging segment, which grew 58.8% over this same time frame to approximately $2.5 billion. Medical professionals as well as consumers are constantly looking for new and improved treatments that provide solutions and preventative care to improve health needs associated with skin issues and skin care in general.

It is therefore desirable to provide a new and improved treatment for actinic purpura, skin disorders, and skin conditions in general. The above discussed limitations in the prior art is not exhaustive. The current invention provides an inexpensive and effective composition and method of treatment for skin not currently found in the known art.

SUMMARY OF THE INVENTION

In view of the foregoing disadvantages inherent in the known types of compositions and methods of treating actinic purpura, skin disorders, and skin conditions in general now present in the prior art, the present invention provides a new and improved effective composition and method of using the same where the prior art fails. As such, the general purpose of the present invention, which will be described subsequently in greater detail, is to provide a new and improved composition and method for the treatment which has all the advantages of the prior art and none of the disadvantages.

To attain this, the present invention essentially comprises a systematic and periodic application of a topical non-toxic formulation that may include ingredients to improve circulation such as but not limited to *arnica* oil CLR and phytotonine; ingredients to thicken the skin such as but not limited to retistar, glycolic acid, vitamin K1, and phyto-age; and ingredients to repair the skin's barrier, such as but not limited to timecode, SKINMIMICS, ABS pomegranate sterols, and pentatavitin. The current invention contemplates the formulation may be utilized in a lotion, cream, liquid, gel, and or combinations thereof and provide an advanced and unique approach to the overall treatment and management.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in this application to the details of construction, arrangement of the components, and amounts thereof set forth in the following description. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception upon which this disclosure is based may readily be utilized as a basis for the designing of other compositions, methods, and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Therefore, it is an object of the present invention to provide a new and improved composition and method of treating actinic purpura, skin disorders, and skin conditions in general that may be easily and effectively used by those afflicted with the symptoms associated with actinic purpura including but not limited to bruising, thin, easily torn skin, and xerosis and may utilize the benefits of the combination of *arnica* oil, glycolic acid, and retinol.

It is a further object of the present invention to provide a new and improved composition and method of treating actinic purpura, skin disorders, and skin conditions in general that may be an essential element in an ideal treatment regimen for hyperkeratotic conditions.

An even further object of the present invention is to provide a new and improved composition and method of treating actinic purpura, skin disorders, and skin conditions in general that is susceptible to a low cost of manufacture with regard to ingredients and associated labor of producing same, and, thus accordingly, is then susceptible to low prices of sale to the consuming public thereby making such economically available.

Still another object of the present invention is to provide a new and improved composition and method of treating actinic purpura, skin disorders, and skin conditions in general which provides all of the advantages of the prior art, while simultaneously overcoming some of the disadvantages normally associated therewith.

Another object of the present invention is to provide a new and improved composition and method of treating actinic purpura, skin disorders, and skin conditions in general that may be used over large areas of skin for those afflicted without or with reduced detrimental side effects.

Yet another object of the present invention is to provide a new and improved composition and method of treating actinic purpura, skin disorders, and skin conditions in general that is commercially available such that public awareness is garnered and those afflicted will have a viable and readily available treatment.

An even further object of the present invention is to provide a new and improved composition and method of treating actinic purpura, skin disorders, and skin conditions in general that combines proven ingredients that have already passed F.D.A. approval.

Still another object of the present invention is to provide a new and improved composition and method of treating actinic purpura, skin disorders, and skin conditions in general that may be utilized in a cream, lotion, liquid, gel and combinations thereof that is non-irritating, fragrance free, and contains no known sensitizing ingredients.

These, together with other objects of the invention, along with the various features of novelty, which characterize the invention, are pointed out with particularity in the claims annexed to and forming a part of this disclosure. For a better understanding of the invention, its operating advantages, and the specific objects attained by its uses, reference should be had to the accompanying descriptive matter in which there are illustrated preferred embodiments of the invention.

DETAILED DESCRIPTION

In a preferred embodiment, the present invention is a composition and method of treatment for actinic purpura, skin disorders, and skin conditions in general through topical systematic and periodic application of a formulation that generally may include ingredients to improve circulation such as but not limited to *arnica* oil CLR and phytotonine; ingredients to thicken the skin such as but not limited to retistar, glycolic acid, vitamin K1, and phyto-age; and ingredients to repair the skin's barrier, such as but not limited to timecode, SKINMIMICS, ABS pomegranate sterols, and pentatavitin. The formulation may be utilized as a cream, lotion, liquid, gel, and combinations thereof and may be utilized as a moisturizer in treating the symptoms associated with solar and or actinic purpura. It is also contemplated that the current invention may be used as a mainstay in the treatment and continued maintenance of the symptoms associated with solar and or actinic purpura as well as a part of a successful treatment regimen specifically formulated for hyperkeratotic skin conditions. It is also understood that the following description of said components is not limited to exact percentages, quantities, or ingredients and that it is understood equivalent ingredients known in the art may be substituted or added.

It is understood that the current invention contemplates use of *arnica* oil which is generally made from *Arnica montana*, known commonly as leopard's bane, wolf's bane, mountain tobacco and mountain *arnica*. It is a European flowering plant with large yellow capitula. *Arnica* is a genus with about 30 perennial, herbaceous species, belonging to the sunflower family Asteraceae). The genus name *Arnica* may be derived from the Greek arna, "lamb," in reference to the soft, hairy leaves.

This circumboreal and montane (subalpine) genus occurs mostly in the temperate regions of western North America, while two are native to Eurasia (*A. angustifolia* and *A. montana*).

The current invention contemplates the utilization of and may utilize the brand of *arnica* oil made by CLR NORTH AMERICA also referred to as "*arnica* oil CLR" although it is understood that other brands, types, and *arnica* sources are contemplated. *Arnica* oil CLR May combine *Glycine Soja* (Soybena) Oil (and) *Arnica Montana* Flower Extract (and) Tocopherol. Generally, *arnica* Oil CLR is a fatty oil extract from *arnica* blossoms.

In a preferred embodiment, the current invention will utilize the benefits of the combination of *arnica* oil, glycolic acid, and retinol. The formulation may include ingredients to help improve microcirculation and strengthen blood vessels, boost production of collagen, elastin, and other proteins associated with skin firmness, and protect the connective tissue from degradation. Furthermore, the current invention may provide a cosmetically pleasing feature with coloring to match the skin tone of non-bruised skin while covering bruised areas. The invention may be applied only once or twice per day depending on the severity of symptoms.

The current invention contemplates a cream, gel, lotion, liquid and combinations thereof of a formulation that may include ingredients to help improve microcirculation and strengthen blood vessels, boost production of collagen, elastin, and other proteins associated with skin firmness, and protect the connective tissue from degradation. It is also contemplated to utilize the formulation with sunscreen. In a preferred embodiment, to prevent further ultraviolet-induced damage to the skin, sunscreens that provide both UV-A and UV-B protection may be applied daily, especially to areas affected by the purpuric lesions. The use of tretinoin may be beneficial in actinic purpura because photo damage is ultimately responsible for this disorder. Tretinoin increases the amount of dermal collagen and decreases the amount of abnormal elastin when applied topically.

The current invention contemplates ingredients to improve circulation such as but not limited to *arnica* oil CLR and phytotonine; ingredients to thicken the skin such as but not limited to retistar, glycolic acid, vitamin K1, and phyto-age; and ingredients to repair the skin's barrier, such as but not limited to timecode, SKINMIMICS, ABS pomegranate sterols, and pentatavitin.

The current invention contemplates a formulation as follows in TABLE 1. It is understood the current invention is not limited to same and the below is for illustrative purposes.

TABLE 1

| TRADE NAME | INCI NAME | CONCENTRATION (W/W) | FUNCTION |
|---|---|---|---|
| | Miscellaneous | QS to 100% | Purified water, thickener, emollients, preservative, fragrance, pH adjuster, etc. |
| Arnica Oil CLR | *Glycine Soja* (Soybean) Oil (and) Arnica Montana Flower Extract (and) Tocopherol | 1% | Arnica extract has a favorable effect on blood flow of peripheral vessels, as well as anti-inflammatory action. It is commonly used to help minimize/prevent bruising. |
| Phytotonine | Propylene Glycol (and) Arnica Montana Flower Extract (and) *Cupressus Sempervirens* Seed Extract (and) Polygonatum Multiflorum Extract | 3% | Plant extracts of Arnica, Cypress, and Solomon's Seal that help to improve microcirculation and strengthen/reinforce vein walls |
| Retistar | Caprylic/Capric Triglyceride (and) Sodium Ascorbate (and) Tocopherol (and) Retinot | 1% | A stabilized oily dispersion of retinot that provides protection against photoaging, improves epithelization, normalizes the physiology of the epidermis, and improves skin pigmentation and barrier function |
| Glycolic Acid | Glycolic Acid | 4% | Continued use promotes skin thickening via stimulating collagen production |
| Vitamin K1 | Phytonadione | 0.001% | Promotes healing of skin discoloration, vascular problems, and scars |

TABLE 1-continued

| TRADE NAME | INCI NAME | CONCENTRATION (W/W) | FUNCTION |
|---|---|---|---|
| Phyto-Age | *Cimicifuga Racemosa* Root Extract | 0.05% | Chinese plant extract that helps redensify the dermis via synthesis of laminin, Type 1 collagen, and GAGS. Its hormone-like activity compensates for decline in estrogen production. |
| Timecode | Palmitoyl Glycine | 1% | Redensifying and anti-inflammatory; promotes microcirculation and improves cellular metabolism |
| SKINMIMICS | Ceteareth-25 (and) Glycerin (and) Cetyl Alcohol (and) Behenic Acid (and) Cholesterol (and) Ceramide NP (and) Ceramide NS (and) Ceramide EOS (and) Ceramide EOP (and) Ceramide AP (and) Caprooyl Phytosphingosine (and) Caprooyl Sphingosine | 2% | Barrier repair and overall water management for mature skin |
| ABS Pomegranate Sterols | *Punica Granatum* Sterols | 1% | Barrier repair and water absorption |
| Pentavitin | Saccharide Isomerate | 3% | Humectant; substantive and durable hydrating effect; effective in low humidity environments and combating irritation associated with AHA use. |
| SymCalmin | Butylene Glycol (and) Pentylene Glycol (and) Hydroxyphenyl Propamidobenzoic Acid | 1% | Anti-itch and anti-redness |
| Niacinamide | Niacinamide | 0.5% | Anti-oxidant, anti-inflammatory, and barrier repair |

Still further, the current invention contemplates a formulation as follows in TABLE 2. It is understood the current invention is not limited to same and the below is for illustrative purposes.

TABLE 2

| CTFA NAME | TRADE NAME | % (W/W) |
|---|---|---|
| Purified Water | Purified Water, USP | 69.849 |
| Cetearyl Alcohol (and) Coco-Glucosides | Montanov 82 | 1.500 |
| *Glycine Soja* (Soybean) Oil (and) Arnica Montana Flower Extract (and) Tocopherol | Arnica Oil CLR | 1.000 |
| Propylene Glycol (and) Arnica Flower Montana Flower Extract (and) *Cupressus Sempervirens* Seed Extract (and) Polygonatum Multiflorum Extract | Phytotonine | 3.000 |
| Glycolic Acid (and) Ammonium Glycolate | Glycolic Compound 4.4 | 4.000 |
| *Cimicifuga Racemosa* Root Extract | Phyto-Age | 0.050 |
| Palmitoyl Glycine | Timecode | 1.000 |
| Ceteareth-25 (and) Glycerin (and) Cetyl Alcohol (and) Behenic Acid (and) Cholesterol (and) Ceramide NP (and) Ceramide NS (and) Ceramide EOS (and) Ceramide EOP (and) Ceramide AP (and) Caprooyl Phytosphingosine (and) Caprooyl Sphingosine | SKINMIMICS | 2.000 |
| Saccharide Isomerate | Pentavitin | 3.000 |
| Butylene Glycol (and) Pentylene Glycol (and) Hydroxyphenyl Propamidobenzoic Acid | SymCalmin | 1.000 |
| Niacinamide | Niacinamide USP | 0.500 |
| Glycerin | Glycerin 99.7% USP Kosher | 1.000 |
| Disodium EDTA | Versene NA | 0.100 |
| Hydroxyethyl acrylate/sodium acryloyldimethyl taurate copolymers | Sepinov EMT 10 | 2.000 |
| Stearyl Alcohol | Stearyl Alcohol | 1.000 |
| *Punica Granatum* (Pomegranate) Sterols | ABS Pomegranate Sterols | 1.000 |
| Caprylic/Capric Triglyceride | Neobee M5 | 1.500 |
| Phytonadione | Vitamin K1 | 0.001 |
| Tocopheryl Acetate | Vitamin E Acetate | 0.200 |
| Polysorbate 20 (and) Retinol | Retinol 50 C | 0.100 |
| Ethylhexylglycerin (and) Phenoxyethanol | Euxyl PE 9010 | 1.000 |
| Propanediol | Zemea Propanediol C/PC | 3.000 |
| Fluorphlogopite (and) Titanium Dioxide | Chione Snowfall White | 0.200 |
| Polyacrylamide (and) C13-14 Isoparaffin (and) Laureth-7 | Sepigel 305 | 2.000 |

The mode of action of the *Arnica* Oil CLR is described as having a favorable effect on the blood flow in peripheral vessels, an anti-inflammatory effect and also a granulating and epithelizing effect on the tissue. Increased circulation and reduced venous congestion are due to the inhibiting effect on aggregation of thrombocytes (3) which is produced by the sesquiterpene lactone contained in *arnica* extracts. The same actives cause the anti-inflammatory effect by inhibiting inflammatory cytokines But also, polysaccharides contained in *arnica* extracts have a modulatory effect on the immune system because they increase phagocytosis and stimulate macrophages.

Herbal active agents have great significance also in pharmacological research. It has been recognized that neither synthesized herbal ingredients nor active substances isolated from plants are equivalent to total complexes extracted from herbs. Synthesis or isolation cannot encompass the multitude of natural accompanying substances that have synergistic properties. The presence of these naturally accompanying substances is what makes effectiveness of complex plant extracts so superior to that of synthesized or isolated individual substances. *Arnica* Oil CLR is a carefully prepared herbal extract, which contains the lipophilic, active constituents of *arnica* blossoms in conjunction with synergistic accompanying substances, thus representing a "total" herbal complex.

SKINMIMICS has proven in-vivo benefits in dry mature skin. It revitalizes dry mature skin by optimizing the total epidermal water management system, repairs the skin's own water protection barrier, activates the skin's own water natural moisturizing system (sphingolipids, filaggrin), and increases the glycerol and water transport mechanism (aquaporin-3). It also contains the recently identified cell-signaling Sphingokine molecules. SKINMIMICS was designed to provide mature skin with three important aspects of skin treatment. Those being protection by correction and repair of membrane defects of the stratum corneum lipid barrier, prevention by supplementation of skin's own precursor substances to finally activate the skin lipid synthesis, and regeneration by stimulation of epidermal renewal and repair (filaggrin, aquaporin 3).

It is a unique multi-lamellar concentrate based on advanced Ceramide technology and the newly identified SPHINGOKINES. SKINMIMICS is a skin-identical equimolar blend of new and unique long chain Ceramides (including Ceramide EOP, EOS, NS, NP and AP) with a broad distribution of fatty acid side-chains, new vegetal based cholesterol and behenic acid. These three types of lipids, essential for protection benefits, are combined with the unique SPHINGOKINES, signaling molecules playing a key role in the prevention and regeneration attributes of SKINMIMICS.

A number of implementations have been described herein. Nevertheless, it will be understood that various modifications may be made. Accordingly, other implementations are within the scope of the following claims. Changes may be made in the combinations, operations, and arrangements of the various parts, elements, and amounts described herein without departing from the spirit and scope of the invention.

We claim:

1. A method for treating actinic purpura in a subject in need thereof comprising applying to the skin of said subject an effective amount of a composition consisting essentially of the following ingredients:

*Arnica montana* flower extract, *Glycine soja* oil, tocopherol, propylene glycol, *Cupressus sempervirens* seed extract, *Polygonatum multiflorum* extract, caprylic/capric triglyceride, sodium ascorbate, retinol, glycolic acid, phytonadione, *Cimicifuga racemosa* root extract, palmitoyl glycine, ceterareth-25, glycerin, cetyl alcohol, behenic acid, cholesterol, ceramide NP, ceramide NS, ceramide EOS, ceramide EOP, ceramide AP, caprooyl phytosphingosine, capryool sphingosine, *Punica granatum* sterols, saccharide isomerate, butylene glycol, pentylene glycol, hydroxyphenyl propamidobenzoic acid, and niacinamide, wherein the ingredients are in amounts effective to treat said actinic purpura.

* * * * *